(12) United States Patent
Burrows

(10) Patent No.: US 7,850,671 B1
(45) Date of Patent: Dec. 14, 2010

(54) DIAPER SYSTEM

(76) Inventor: Kimberley A. Burrows, #7 Apartment #3 Middletown Road, Pembroke (BM) HM17

( * ) Notice: Subject to any disclaimer, the term of this patent is extended or adjusted under 35 U.S.C. 154(b) by 798 days.

(21) Appl. No.: 11/811,009

(22) Filed: Jun. 8, 2007

(51) Int. Cl.
*A61F 13/15* (2006.01)
*A61F 13/20* (2006.01)

(52) U.S. Cl. .............................. 604/385.06
(58) Field of Classification Search .......... 604/291, 604/359, 360, 385.06
See application file for complete search history.

(56) References Cited

U.S. PATENT DOCUMENTS 4,221,221 A * 9/1980 Ehrlich ................... 604/386
5,569,230 A * 10/1996 Fisher et al. ........... 604/385.06
7,021,848 B1 * 4/2006 Gruenbacher et al. .......... 401/1

* cited by examiner

*Primary Examiner*—Melanie J Hand

(57) ABSTRACT

A diaper system for distributing a rash inhibiting powdered material onto a pelvic area of a child includes a diaper being worn around the pelvic area of the child. The diaper includes a front edge positioned around a front of the pelvic area and a rear edge positioned around a back of the pelvic area when the diaper is worn. A pouch is coupled to an interior surface of the diaper. The pouch is positioned in a closed state when the diaper is folded in half. The pouch is opened when the diaper is opened to be placed on the child. A rash inhibiting powdered material is positioned in the pouch when the diaper is folded in half. The powdered material is exposed during opening of the diaper and distributed on the pelvic area of the child to inhibit diaper rash when the diaper is placed on the child.

9 Claims, 3 Drawing Sheets

DIAPER SYSTEM

BACKGROUND OF THE INVENTION

1. Field of the Invention

The present invention relates to powder dispensing diapers and more particularly pertains to a new powder dispensing diaper for distributing a rash inhibiting powdered material onto a pelvic area of a child.

2. Description of the Prior Art

The use of powder dispensing diapers is known in the prior art. While these devices fulfill their respective, particular objectives and requirements, the need remains for a system that has certain improved features that positions a rash inhibiting powdered material along a portion of the length of the system to provide the greatest coverage of a pelvic area of a child. Additionally, the system should include a pouch to contain the rash inhibiting powdered material that is liquid permeable to allow the excretions of the child to pass through the pouch.

SUMMARY OF THE INVENTION

The present invention meets the needs presented above by generally comprising a diaper being worn around a pelvic area of a child. The diaper includes a front edge positioned around a front of the pelvic area when the diaper is worn. The diaper includes a rear edge positioned around a back of the pelvic area when the diaper is worn. A pouch is coupled to an interior surface of the diaper. The pouch is positioned in a closed state when the diaper is folded in half. The pouch is opened when the diaper is opened to be placed on the child. The pouch extends along a portion of a length of the diaper between the front edge and the rear edge. A rash inhibiting powdered material is positioned in the pouch when the diaper is folded in half. The powdered material is exposed during opening of the diaper. The powdered material is distributed on the pelvic area of the child to inhibit diaper rash when the diaper is placed on the child. The powdered material is moisture absorbent to inhibit moisture being trapped against the pelvic area.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
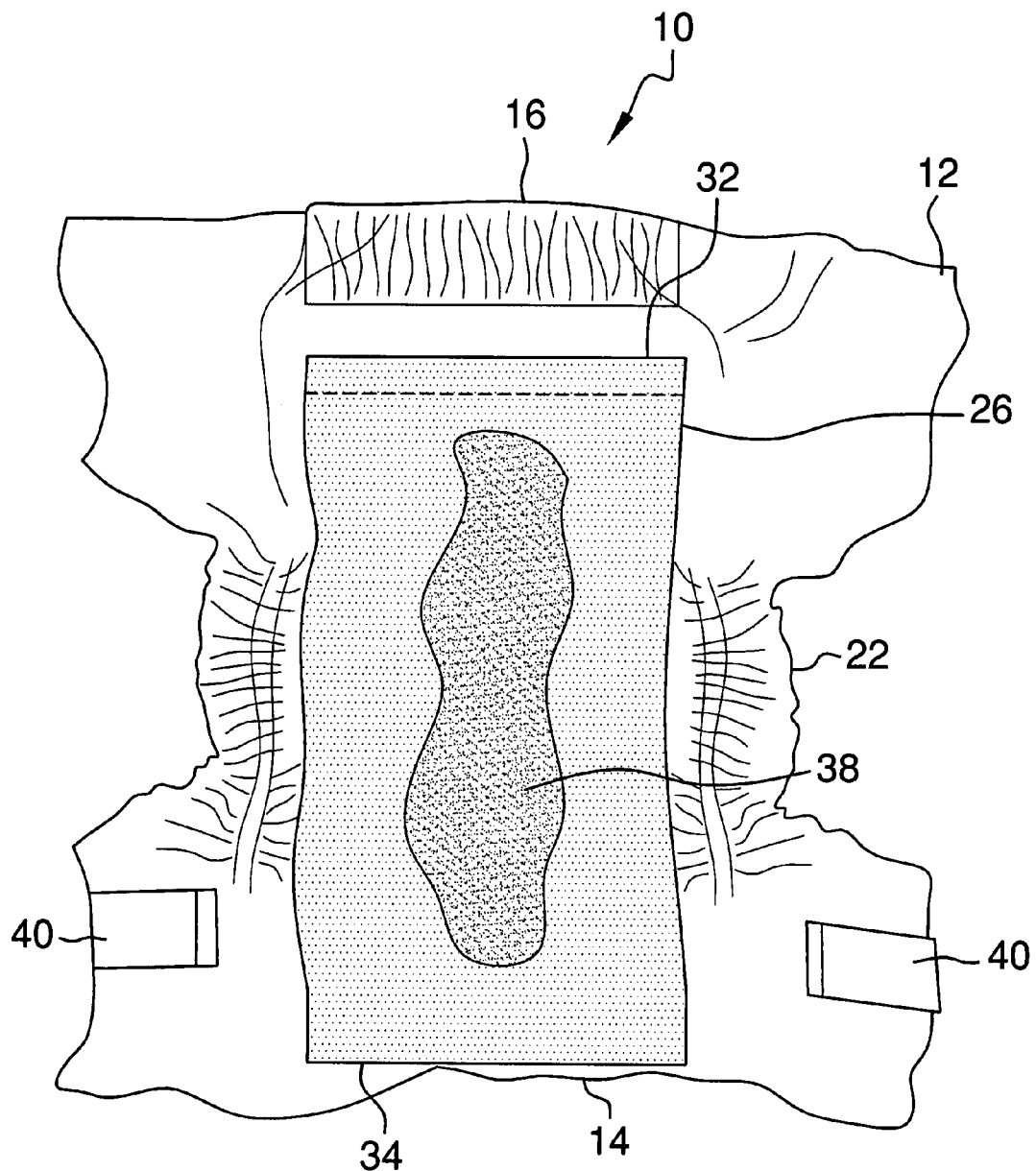
FIG. 1 is a top view of a diaper system according to the present invention when the diaper is opened.
Figure 2:
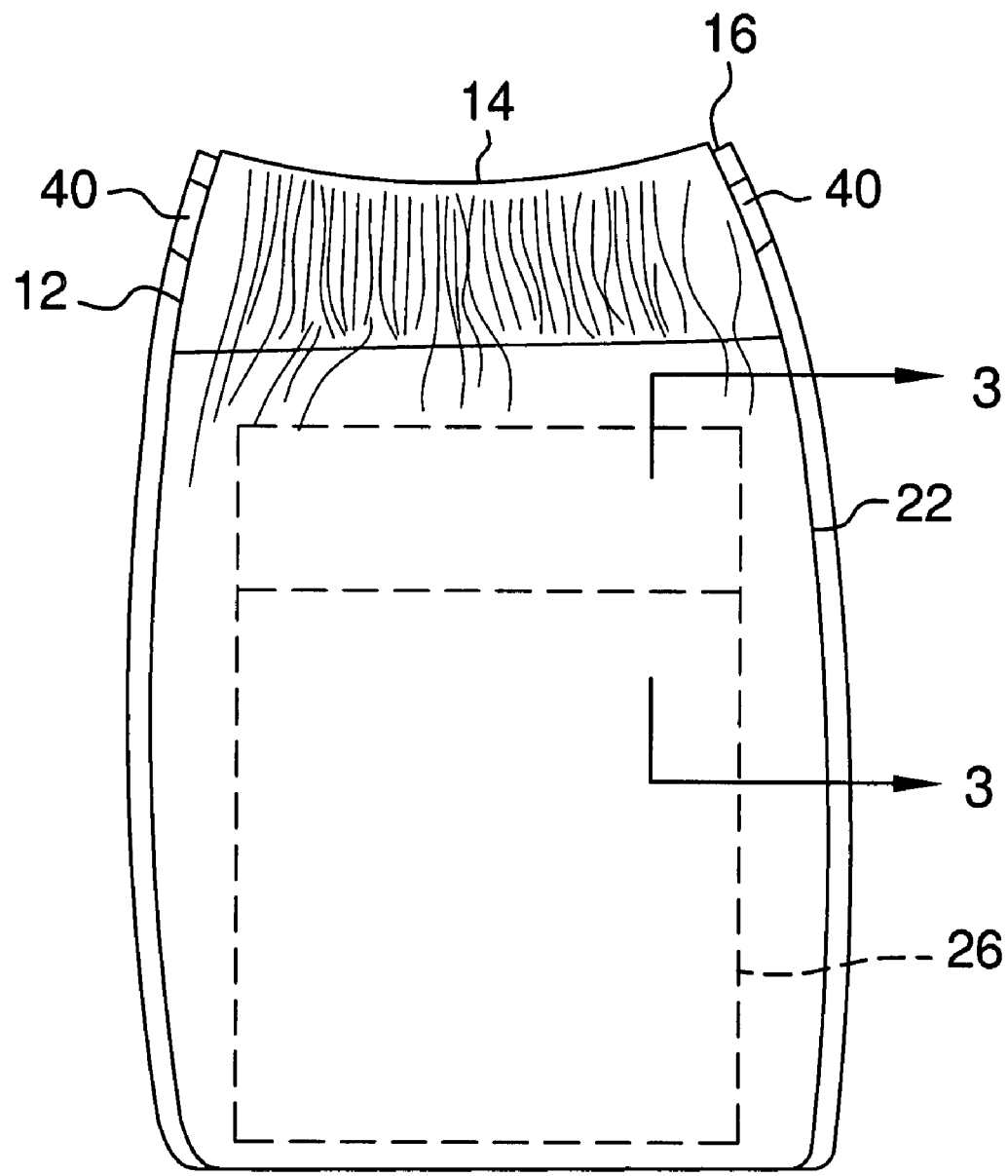
FIG. 2 is a top view of the present invention when the diaper is folded.
Figure 3:
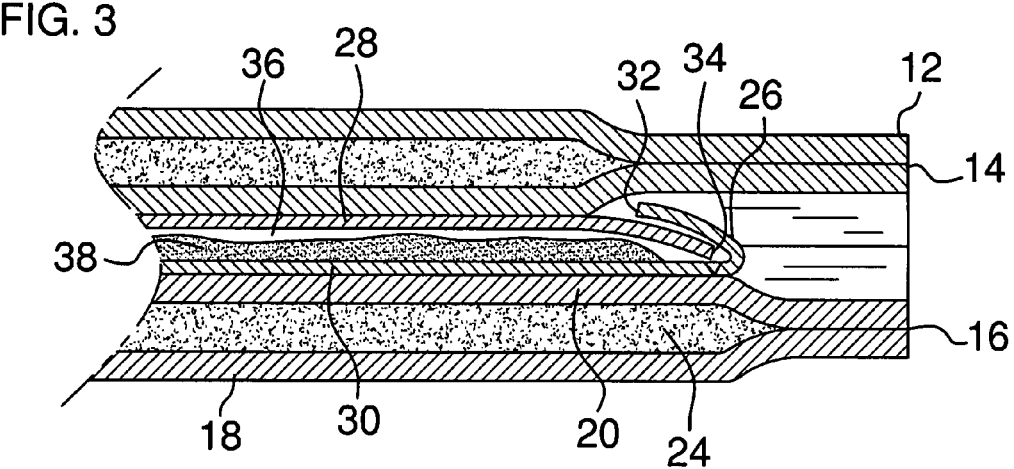
FIG. 3 is a cross-sectional view of the present invention taken along line 3-3 of FIG. 2.
Figure 4:
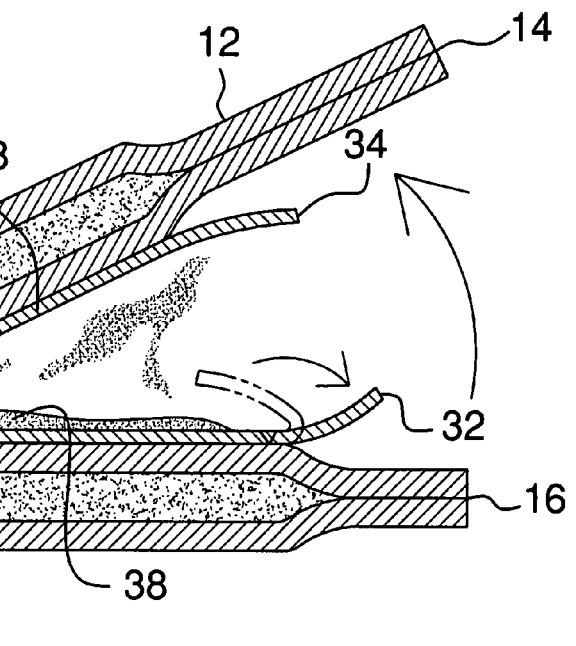
FIG. 4 is the cross-sectional view of the present invention shown in FIG. 3 as the diaper is being opened.

With reference now to the drawings, and in particular to FIGS. 1 through 4 thereof, a new powder dispensing diaper embodying the principles and concepts of the present invention and generally designated by the reference numeral 10 will be described.

As best illustrated in FIGS. 1 through 4, the diaper system 10 generally comprises a diaper 12 being worn around a pelvic area of a child. The diaper 12 includes a front edge 14 positioned around a front of the pelvic area when the diaper 12 is being worn. The diaper 12 includes a rear edge 16 positioned around a back of the pelvic area when the diaper 12 is being worn. The diaper 12 includes an outer layer 18 comprised of a liquid impermeable material to inhibit the fluids excreted by the child from soaking through the outer layer 18.

The diaper 12 also includes an interior layer 20 comprised of a liquid permeable material to permit the fluids excreted by the child to pass through the interior layer 20. The interior layer 20 and the exterior layer are coupled to one another along a peripheral edge 22 of the diaper 12. An absorbent layer 24 is positioned between the interior layer 20 and the exterior layer. The absorbent layer 24 absorbs the fluids secreted by the child when the fluid passes through the interior layer 20.

A pouch 26 is coupled to the interior layer 20 of the diaper 12. The pouch 26 is positioned in a closed state when the diaper 12 is folded in half. The pouch 26 is opened when the diaper 12 is opened to be placed on the child. The pouch 26 extends along a portion of a length of the diaper 12 between the front edge 14 and the rear edge 16. The pouch 26 is comprised of a fluid permeable material to permit fluids excreted from the child to pass through the pouch 26 when the diaper 12 is being worn. The pouch 26 includes a forward wall 28. A portion of the forward wall 28 is coupled to the diaper 12 adjacent the front edge 14.

The pouch 26 additionally includes a back wall 30. A portion of the back wall 30 is coupled to the diaper 12 adjacent the rear edge 16. A back edge 32 of the pouch 26 is folded over a forward edge 34 of the pouch 26 to form a containment space 36 between the forward wall 28 and the back wall 30 when the diaper 12 is folded in half. The forward wall 28 and the back wall 30 are separated to expose the containment space 36 when the diaper 12 is opened.

A rash inhibiting powdered material 38 is positioned in the pouch 26 when the diaper 12 is folded in half. The powdered material 38 is exposed during opening of the diaper 12. The powdered material 38 is distributed on the pelvic area of the child to inhibit diaper rash when the diaper 12 is placed on the child. The powdered material 38 is moisture absorbent to inhibit moisture being trapped against the pelvic area. The powdered material 38 is positioned in the containment space 36 of the pouch 26.

A pair of tabs 40 is coupled to the diaper 12 adjacent the front edge 14 of the diaper 12. The tabs 40 are adhered to the diaper 12 adjacent the rear edge 16 of the diaper 12 to secure the diaper 12 around the pelvic area of the child when the diaper 12 is being worn.

In use, the diaper 12 is opened from the folded state. As the diaper 12 is opened the pouch 26 is also opened and the powdered material 38 exposed. The diaper 12 is then positioned around the pelvic area of the child with the front edge 14 around a front of the pelvic area and the back edge 32 around a back of the pelvic area. The tabs 40 are then secured to the diaper 12 adjacent the back edge 32 to secure the diaper 12 to the child.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A diaper system for covering a pelvic area of a child to collect fluids excreted from the child, said system comprising:
    a diaper being worn around the pelvic area of the child, said diaper including a front edge being positioned around a front of the pelvic area when the diaper is being worn, said diaper including a rear edge being positioned around a back of the pelvic area when the diaper is being worn;
    a pouch being coupled to an interior layer of said diaper, said pouch being positioned in a closed state when said diaper is folded in half, said pouch being opened when said diaper is opened to be placed on the child, said pouch extending along a portion of a length of said diaper between said front edge and said rear edge, said pouch including a forward wall, a portion of said forward wall being coupled to said diaper adjacent said front edge; and
    a rash inhibiting powdered material being positioned in said pouch when said diaper is folded in half, said powdered material being exposed during opening of said diaper, said powdered material being distributed on the pelvic area of the child to inhibit diaper rash when said diaper is placed on the child, said powdered material being moisture absorbent to inhibit moisture being trapped against the pelvic area.

2. The system according to claim 1, wherein said diaper includes an outer layer being comprised of a liquid impermeable material to inhibit the fluids excreted by the child from soaking through said outer layer.

3. The system according to claim 2, wherein said interior layer is comprised of a liquid permeable material to permit the fluids excreted by the child to pass through said interior layer, said interior layer and said exterior layer being coupled to one another along a peripheral edge of said diaper.

4. The system according to claim 3, wherein said diaper includes an absorbent layer being positioned between said interior layer and said exterior layer, said absorbent layer absorbing the fluids secreted by the child when the fluid passes through said interior layer.

5. The system according to claim 1, wherein said pouch is comprised of a fluid permeable material to permit fluids excreted from the child to pass through said pouch when said diaper is being worn.

6. The system according to claim 1, wherein said pouch includes a back wall, a portion of said back wall being coupled to said diaper adjacent said rear edge.

7. The system according to claim 6, wherein a back edge of said pouch is folded over a forward edge of said pouch to form a containment space between said forward wall and said back wall when said diaper is folded in half, said forward wall and said back wall being separated to expose said containment space when said diaper is opened, said powdered material being positioned in said containment space of said pouch.

8. The system according to claim 1, further comprises a pair of tabs being coupled to said diaper adjacent said front edge of said diaper, said tabs being adhered to said diaper adjacent said rear edge of said diaper to secure said diaper around the pelvic area of the child when said diaper is being worn.

9. A diaper system for covering a pelvic area of a child to collect fluids excreted from the child, said system comprising:
    a diaper being worn around the pelvic area of the child, said diaper including a front edge being positioned around a front of the pelvic area when the diaper is being worn, said diaper including a rear edge being positioned around a back of the pelvic area when the diaper is being worn, said diaper including an outer layer being comprised of a liquid impermeable material to inhibit the fluids excreted by the child from soaking through said outer layer, said diaper including an interior layer being comprised of a liquid permeable material to permit the fluids excreted by the child to pass through said interior layer, said interior layer and said exterior layer being coupled to one another along a peripheral edge of said diaper, an absorbent layer being positioned between said interior layer and said exterior layer, said absorbent layer absorbing the fluids secreted by the child when the fluid passes through said interior layer;
    a pouch being coupled to said interior layer of said diaper, said pouch being positioned in a closed state when said diaper is folded in half, said pouch being opened when said diaper is opened to be placed on the child, said pouch extending along a portion of a length of said diaper between said front edge and said rear edge, said pouch being comprised of a fluid permeable material to permit fluids excreted from the child to pass through said pouch when said diaper is being worn, said pouch comprising;
        a forward wall, a portion of said forward wall being coupled to said diaper adjacent said front edge;
        a back wall, a portion of said back wall being coupled to said diaper adjacent said rear edge;
        a back edge of said pouch being folded over a forward edge of said pouch to form a containment space between said forward wall and said back wall when said diaper is folded in half, said forward wall and said back wall being separated to expose said containment space when said diaper is opened;
    a rash inhibiting powdered material being positioned in said pouch when said diaper is folded in half, said powdered material being exposed during opening of said diaper, said powdered material being distributed on the pelvic area of the child to inhibit diaper rash when said diaper is placed on the child, said powdered material being moisture absorbent to inhibit moisture being trapped against the pelvic area, said powdered material being positioned in said containment space of said pouch; and
    a pair of tabs being coupled to said diaper adjacent said front edge of said diaper, said tabs being adhered to said diaper adjacent said rear edge of said diaper to secure said diaper around the pelvic area of the child when said diaper is being worn.

* * * * *